US00PP10531P

United States Patent [19]

Pouw

[11] Patent Number: Plant 10,531

[45] Date of Patent: Aug. 4, 1998

[54] HYBRID TEA ROSE PLANT NAMED 'RUIJAMU'

[75] Inventor: A. A. Pouw, Pl de Kwakel, Netherlands

[73] Assignee: De Ruiter's Nieuwe Rozen B.V., De Kwakel, Netherlands

[21] Appl. No.: 759,604

[22] Filed: Dec. 5, 1996

[51] Int. Cl.[6] ..... A01H 5/00

[52] U.S. Cl. ..... Plt./16

[58] Field of Search ..... Plt./11, 15, 16

*Primary Examiner*—Howard J. Locker

*Attorney, Agent, or Firm*—Christie, Parker & Hale, LLP

[57] ABSTRACT

A new variety of hybrid tea rose plant producing light yellow to orange bicolor flowers of good form and suitable for growing under glass.

1 Drawing Sheet

BACKGROUND OF THE INVENTION

The present invention relates to a new and distant variety of rose plant of the hybrid tea rose class which was discovered as a natural mutation in a controlled planting of 'Ruirovingt' in De Kwakel, Holland. The varietal denomination of the new variety is 'Ruijamu'. The new variety was isolated and asexually reproduced by budding in Holland.

SUMMARY OF THE INVENTION

Among the novel characteristics possessed by this new variety which distinguish it from its parent and all other varieties of which I am aware are its attractive light yellow to orange blend bicolor flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in Holland shows that the foregoing and other distinguishing characteristics come true to form and are established and transmitted through succeeding propagations.

Comparison with Parent

'Ruijamu' is a mutation out of 'Ruirovingt' (U.S. Plant Pat. No. 8,528) differing only in the color of the flower. The color of 'Ruirovingt' is a mix of pink, yellow, cream and the color of 'Ruijamu' is a mix of yellow, orange, pink.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Mutation of 'Ruirovingt'.
Class: Hybrid Tea.

As can be seen in the accompanying detail illustration there is shown a new shoot and green bud, 1; compound three, five and seven leaflet leaves, 2, 3 and 4, respectively; a stem, 5; buds, 6, 7 and 8; a flower, 9, and flower stems 10, 11 and 12, with productive organs displayed.

The following further horticultural description is based on observations made of specimens grown under glass in Holland.

Flower

Blooming habit: Nearly continuous.

A. Bud:

(1) *Size.*—Medium, about 3 to 4 cm long and about 2 to 3 cm wide.

(2) *Form.*—Ovate (shape of longitudinal section just before separation of sepals); urn-shaped after sepals part.

(3) *Color.*—As sepals divide, near 170B, with yellow toward point of attachment.

(4) *Sepals.*—About length of bud, some foliated, lower surface coloration of sepals near 144A with some anthocyan coloring (red brown); upper surface coloration of sepals near 148C.

(5) *Peduncle.*—About 9 cm, erect, very strong. Color near 138B to near 147C; few hairs or prickles.

B. Bloom:

*Flower.*—Medium; viewed from above — round; viewed from side — (a) upper part of fully opened flower, flat; (b) lower part of fully opened flower, flattened convex.

(1) *Size.*—Average size when fully expanded — about 7 to 8 cm.

(2) *Borne.*—Singly, one to a stem.

(3) *Form.*—Exhibition type, somewhat flat top, spiral imbricated, puter petals reflex somewhat to points and curl under, inner petals have weak undulation at margin.

(4) *Petalage.*—About 25; about 14 petaloids, about 3×3 cm.

(5) *Color.*—After sepals part and petals unfurl color of petal undersurface visible is near 170B to 33C; as flowers open orange color remains prominent until flower is fully open; open flower shows petal upper surface, outer petals near 159B to 159C; color where petals bunch is near 19B to 19C. Some outer petals have near 9B on inner surface and near 11B on outer surface, flushes of white with pink tones. Overall tonality from a distance is attractive orange to light yellow blend (Apricot-orange).

(6) *Peduncle.*—Generally smooth, as bloom ages petals become grey/white and light pink, near 65D.

(7) *Fragrance.*—Weak.

(8) *Length of stem**.—About 50 cm from last cut.

(9) *Production**.—About 240 blooms/$m^2$/year.

*Average, actual depends on circumstances of cultivation.

Petals:

(1) *Texture.*—Crisp.

(2) *Appearance.*—Inside velvety and outside satiny.

(3) *Form and size.*—Broad, medium, weak undulation of margin.

(4) *Arrangement.*—Regularly arranged, imbricated.

(5) *Petaloids.*—Several, about 14.

(6) *Lasting quality.*—Vaselife varies from about 15 to 20 days; blooming on plant can be more than 30 days; flower fades and the color become greenish.

Reproductive Organs

A. Stamens, filaments and anthers:

*Arrangement and color.*—Regularly arranged around styles; color of filaments — yellow.

B. Pollen:

*Color.*—Near 15D.

C. Styles: Long, stigma above mouth of receptacle, yellow.

D. Stigmas: Yellow, positioned below anthers.

E. Hip: Pitcher-shaped; medium seed vessel at petal fall but few set seed; when seed sets hip is about 1.5 cm and green-orange color.

Plant

A. Form: Narrow, bushy, average disease resistance.

B. Growth: Vigorous, about 1.0 m in height, about 0.5 m in width.

C. Foliage: Compound 3, 5 and 7 leaflets.

(1) *Size.*—About 15–20 cm; length about 5.5–6 cm; veins are visible, often purple.

(2) *Quantity.*—Abundant.

(3) *Color.*—Juvenile foliage — red purple to bronze-reddish brown; near 183A to 183B; weak anthocyanin coloration, (shoot about 20 cm long); mature leaf color — dark green, near 147A, undersurface near 138A.

(4) *Shape.*—Elliptic.

(5) *Texture.*—Upper side is medium glossy; underside is matte.

(6) *Edge.*—Serrate.

(7) *Serration.*—Serrate to double serrate.

(8) *Leaf stem.*—Color — medium green, near 147A to 147B.

(9) *Stipules.*—Variable, short to long, variable margins, medium green with dark edge and/or tips, distinct auricle.

(10) *Leaflets.*—Cross section — slight concave: strong undulation of margin; terminal leaflet — terminal leaflet 3- leaflet leave, 8 to 9 cm; 5- leaflet leave, 6 to 7 cm; 7- leaflet leaf, 4 to 5 cm, wedge-shaped base.

D. Wood:

(1) *New wood.*—Color — near 172B, young shoots have weak anthocyanin; shiny.

(2) *Old wood.*—Color — near 147A to 147B, somewhat dull.

E. Prickles (thorns):

(1) *Prickles.*—Present; quantity (main stalk) — Ordinary; shape of lower side — concave; Length — short prickles absent or very few, long prickles medium; Position — irregular.

F. Disease resistance: Some susceptibility to powdery and downy mildew.

What is claimed is:

1. A new and distinct variety of rose plant of the hybrid tea rose class, substantially as shown and described.

* * * * *

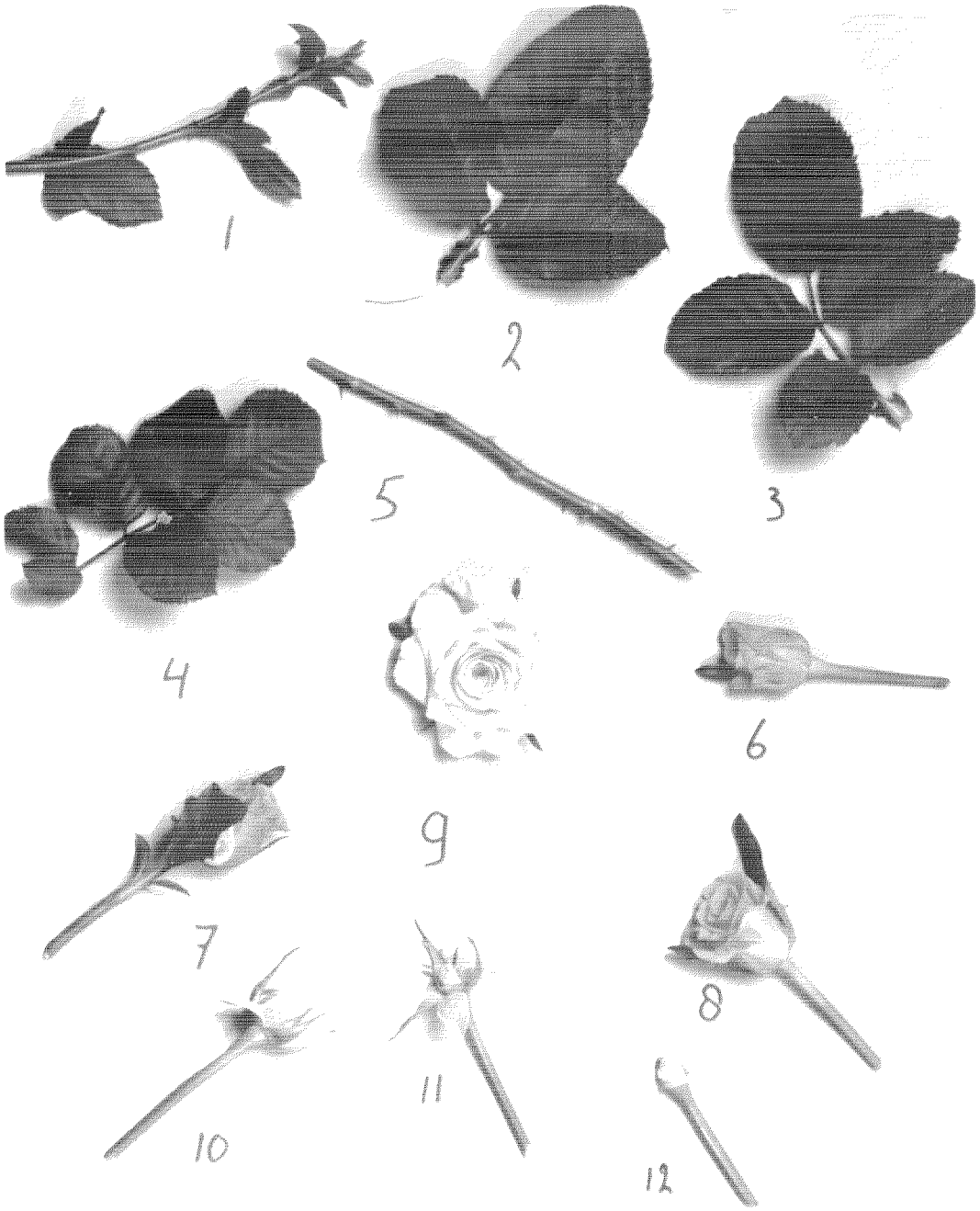
1
2
3
4
5
6
7
8
9
10
11
12